-

US011148126B2

(12) United States Patent
Kim et al.

(10) Patent No.: US 11,148,126 B2
(45) Date of Patent: *Oct. 19, 2021

(54) CATALYST SYSTEM FOR OLEFIN OLIGOMERIZATION AND METHOD FOR PREPARING OLEFIN OLIGOMER BY USING SAME

(71) Applicant: LOTTE CHEMICAL CORPORATION, Seoul (KR)

(72) Inventors: Tae Jin Kim, Daejeon (KR); Hee Young Kim, Daejeon (KR); Seung Woong Yoon, Daejeon (KR)

(73) Assignee: LOTTE CHEMICAL CORPORATION, Seoul (KR)

(*) Notice: Subject to any disclaimer, the term of this patent is extended or adjusted under 35 U.S.C. 154(b) by 0 days.

This patent is subject to a terminal disclaimer.

(21) Appl. No.: 16/845,277

(22) Filed: Apr. 10, 2020

(65) Prior Publication Data

US 2020/0238264 A1 Jul. 30, 2020

Related U.S. Application Data

(63) Continuation of application No. PCT/KR2018/011980, filed on Oct. 11, 2018.

(30) Foreign Application Priority Data

Oct. 11, 2017 (KR) .......... 10-2017-0130250
Nov. 1, 2017 (KR) .......... 10-2017-0144723

(51) Int. Cl.
*B01J 31/18* (2006.01)
*B01J 31/04* (2006.01)
*B01J 31/14* (2006.01)
*C07C 2/32* (2006.01)

(52) U.S. Cl.
CPC .......... *B01J 31/1815* (2013.01); *B01J 31/04* (2013.01); *B01J 31/143* (2013.01); *C07C 2/32* (2013.01); *B01J 2231/20* (2013.01); *B01J 2531/004* (2013.01); *B01J 2531/31* (2013.01); *C07C 2531/14* (2013.01)

(58) Field of Classification Search
CPC ........ B01J 31/182; B01J 23/26; B01J 31/143; B01J 31/2234; B01J 31/122; B01J 2331/20; B01J 2531/004; B01J 2531/007; B01J 2531/0205; B01J 2531/31; B01J 2531/62; C07C 2/32; C07C 2/34; C07C 2531/14; C07C 2531/22; C07F 5/066

See application file for complete search history.

(56) References Cited

U.S. PATENT DOCUMENTS

| 5,376,612 A | 12/1994 | Reagen et al. |
| 5,563,312 A | 10/1996 | Knudsen et al. |
| 5,750,817 A | 5/1998 | Tanaka et al. |
| 2005/0187391 A1* | 8/2005 | Knudsen ............... C07C 2/32 548/402 |
| 2007/0043181 A1* | 2/2007 | Knudsen ............... B01J 31/18 526/104 |
| 2017/0313634 A1* | 11/2017 | Brown .................. B01J 31/188 |
| 2018/0071725 A1* | 3/2018 | Klosin ................. B01J 31/2208 |

FOREIGN PATENT DOCUMENTS

| KR | 2012-0112590 A | 10/2012 |
| KR | 2015-0037581 A | 4/2015 |
| KR | 2016-0062525 A | 6/2016 |
| KR | 2016-0063106 A | 6/2016 |
| KR | 2018-0032244 A | 3/2018 |
| WO | 2015/133805 A1 | 9/2015 |

OTHER PUBLICATIONS

International Search Report issued in International Application No. PCT/KR2018/011980 dated Feb. 8, 2019 (2 pages).
Written Opinion issued in International Application No. PCT/KR2018/011980 dated Feb. 8, 2019 (5 pages).

* cited by examiner

Primary Examiner — Ali Z Fadhel
(74) Attorney, Agent, or Firm — Osha Bergman Watanabe & Burton LLP

(57) ABSTRACT

Disclosed are a catalyst system capable of selectively oligomerizing olefins including ethylene and a method for preparing an olefin oligomer by using the same and, specifically, a novel catalyst system capable of trimerizing and tetramerizing olefins, unlike olefin oligomerization catalyst systems that have been reported so far, and a method for preparing an olefin oligomer by using the same. The present invention provides a catalyst system for olefin oligomerization, the catalyst system comprising: a ligand compound represented by chemical formula 1; a chromium compound; a metal alkyl compound; and an aliphatic or alicyclic hydrocarbon solvent.

12 Claims, No Drawings

CATALYST SYSTEM FOR OLEFIN OLIGOMERIZATION AND METHOD FOR PREPARING OLEFIN OLIGOMER BY USING SAME

TECHNICAL FIELD

The present invention relates to a catalyst system for olefin oligomerization and a method for preparing an olefin oligomer by using the same, and more particularly, a novel catalyst system capable of trimerizing and tetramerizing olefins, and a method for preparing an olefin oligomer by using the same.

BACKGROUND ART

A linear alpha-olefin is widely used commercially as an important material used in comonomers, cleaning agents, lubricants, plasticizers, and the like, and in particular, 1-hexene and 1-octene are frequently used as comonomers for controlling the density of polyethylene in preparation of linear low density polyethylene (LLDPE), etc.

Specifically, in the previously known process of preparing LLDPE, a branch is formed in the polymer backbone with ethylene to be copolymerized with a comonomer such as an alpha-olefin, for example, 1-hexene or 1-octene, in order to control the density. Therefore, when LLDPE having a high comonomer content is produced, the price of the comonomer may occupy a great part of the production cost. Therefore, various attempts have been made to reduce the production cost of the comonomer. In addition, since the alpha-olefin has different application fields or market size according to kinds thereof, technologies for selectively producing specific alpha-olefins are very commercially important, and recently, research has been conducted on chromium catalyst technologies for producing 1-hexene, 1-octene, and the like, with high selectivity through selective ethylene oligomerization.

For example, as a catalyst system for preparing 1-hexene, etc. by polymerizing olefins such as ethylene, and the like, a high activity, high-selectivity ethylene trimerization catalyst system using a chromium trivalent compound, a pyrrole compound, a non-hydrolyzed aluminum alkyl, and an unsaturated hydrocarbon was published from Philips Co. in 1994 (see U.S. Pat. No. 5,376,612), and then 1-hexene was commercially produced from the above catalyst system from 2003. Among various chromium trivalent compounds, a catalyst system using tris(2-ethylhexanoate) chromium(III) ($Cr(EH)_3$, $EH=O_2C_8H_{15}$) showed particularly excellent catalytic activity, and a catalyst system using $Cr(EH)_3$ was intensively studied and commercialized.

The catalyst system using $Cr(EH)_3$ may be prepared in an unsaturated hydrocarbon solvent, for example, by adding a mixed solution of triethyl aluminum and ethyl aluminum dichloride to an unsaturated hydrocarbon solvent (such as toluene) in which $Cr(EH)_3$ and 2, 5-dimethylpyrrole are mixed. Typically, since the trimerization reaction of olefin is carried out in a saturated hydrocarbon solvent such as cyclohexane, the unsaturated hydrocarbon solvent of the prepared catalyst system should be removed by vacuum decompression and then dissolved in the saturated hydrocarbon solvent such as cyclohexane and then used, or the prepared unsaturated hydrocarbon solution phase catalyst system should be used for the trimerization reaction and the unsaturated hydrocarbon solvent used for the catalyst preparation should be separated and removed after the reaction is completed. In addition, when preparing a catalyst using $Cr(EH)_3$, a black precipitate is formed as a by-product while a catalyst activating species is formed, and thus a process of filtering the black precipitate is required (see U.S. Pat. No. 5,563,312). A process of removing an unsaturated hydrocarbon solvent such as toluene, a process of filtering, etc. may be a burden in commercialization. In order to omit the process of removing an unsaturated hydrocarbon solvent, when the catalyst system is prepared in an aliphatic hydrocarbon solvent such as cyclohexane which is subjected to a trimerization reaction, thermal stability of the prepared catalyst is lowered, and thus, the catalyst is inactivated during the trimerization reaction or catalyst selectivity is lowered to form a large amount of side reactants in addition to olefin trimer (see U.S. Pat. No. 5,563,312), and an unsaturated hydrocarbon is included as an essential component in the catalyst system from Philips Co., Ltd.

Therefore, International Patent Publication No. WO2015/133805 discloses a catalyst system having excellent catalytic activity during olefin polymerization (trimerization) and a raw material compound of the catalyst system capable of preparing the catalyst system in a saturated hydrocarbon solvent without a need of a filtration process due to the absence of byproduct generated during catalyst preparation.

However, there is a problem that, in all of the prior patents, only the trimerization is selectively conducted in the process of performing the olefin oligomerization.

DISCLOSURE OF THE INVENTION

Technical Problem

The present invention provides a catalyst system capable of selectively oligomerizing olefins including ethylene and a method for preparing an olefin oligomer by using the same, and specifically, a novel catalyst system capable of trimerizing and tetramerizing olefins, unlike olefin oligomerization catalyst systems that have been reported so far, and a method for preparing an olefin oligomer by using the same.

Technical Solution

To solve the above problem, the present invention provides a catalyst system for olefin oligomerization, the catalyst system including: a ligand compound represented by Chemical Formula 1 below; a chromium compound; a metal alkyl compound; and an aliphatic or alicyclic hydrocarbon solvent.

[Chemical Formula 1]

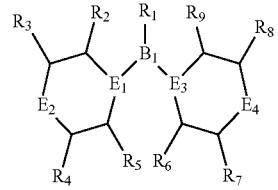

In Chemical Formula 1, $E_1$ and $E_3$ are boron (B), carbon (C), nitrogen (N), silicon (Si), or phosphorus (P), and $E_2$ and $E_4$ are boron (B), carbon (C), nitrogen (N), oxygen (O), silicon (Si), phosphorus (P), or sulfur (S), except that both $E_1$ and $E_2$ are carbon (C) and both $E_3$ and $E_4$ are carbon (C), $B_1$ is aluminum (Al), boron (B), nitrogen (N), or phosphorus (P), $R_1$ to $R_9$ are each independently hydrogen, an alkyl group having 1 to 20 carbon atoms, a cycloalkyl group having 3 to 20 carbon atoms, an alkylsilyl group having 1 to carbon atoms, a haloalkyl group having 1 to 20 carbon atoms, an aryl group having 6 to 40 carbon atoms, an arylalkyl group having 7 to 20 carbon atoms, an arylsilyl group having 6 to 20 carbon atoms, an alkylaryl group having 7 to 20 carbon atoms, an aryloxy group having 6 to 20 carbon atoms, a halogen group, or an amino group.

In addition, in Chemical Formula 1 above, there is provided a catalyst system characterized in that $E_1$ may be nitrogen (N) and E2 may be oxygen (O), or $E_3$ may be nitrogen (N) and $E_4$ may be oxygen (O).

Furthermore, there is provided a catalyst system characterized in that the chromium compound may be a compound containing chromium(III) or chromium(II).

In addition, there is provided a catalyst system characterized in that the metal alkyl compound may be at least one selected from the group consisting of an alkylaluminum compound, an alkylboron compound, an alkylmagnesium compound, an alkylzinc compound, and an alkyllithium compound.

Further, there is provided a catalyst system characterized in that the molar ratio of the ligand compound, the chromium compound, and the metal alkyl compound may be 0.5:1:1 to 10:1:10,000 with respect to the chromium compound.

Moreover, there is provided a catalyst system characterized in that the aliphatic or alicyclic hydrocarbon solvent may be an aliphatic or alicyclic hydrocarbon solvent having 5 to 13 carbon atoms.

In addition, there is provided a catalyst system characterized in that the alicyclic hydrocarbon solvent may be a cycloalkene having 5 to 13 carbon atoms.

Furthermore, there is provided a catalyst system characterized in that the aliphatic or alicyclic hydrocarbon solvent may be n-heptane, 2-methyl hexane, 3-methyl hexane, 3-ethyl pentane, 2,3-dimethyl pentane, 2,4-dimethyl pentane, 2,2-dimethyl pentane, 3,3-dimethyl pentane, 2,2,3-trimethyl butane, cyclopropene, cyclobutene, cyclopentene, cyclopentane, cyclohexene, cycloheptane, cycloheptene, cyclooctane, cyclooctene, cyclononene, cyclodecane, cyclodecene, or a mixture thereof.

In addition, there is provided a catalyst system characterized in that the olefin oligomerization may include a trimerization and a tetramerization.

According to another aspect of the present invention, there is provided a method for preparing an olefin oligomer, the method including oligomerizing olefins in an inert solvent that does not react with a catalyst system in the presence of the catalyst system for olefin oligomerization including: a ligand compound represented by Chemical Formula 1 below; a chromium compound; a metal alkyl compound; and an aliphatic or alicyclic hydrocarbon solvent.

[Chemical Formula 1]

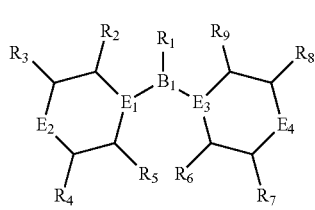

In Chemical Formula 1, $E_1$ and $E_3$ are boron (B), carbon (C), nitrogen (N), silicon (Si), or phosphorus (P), and $E_2$ and $E_4$ are boron (B), carbon (C), nitrogen (N), oxygen (O), silicon (Si), phosphorus (P), or sulfur (S), except that both $E_1$ and $E_2$ are carbon (C) and both $E_3$ and $E_4$ are carbon (C), $B_1$ is aluminum (Al), boron (B), nitrogen (N), or phosphorus (P), $R_1$ to $R_9$ are each independently hydrogen, an alkyl group having 1 to 20 carbon atoms, a cycloalkyl group having 3 to 20 carbon atoms, an alkylsilyl group having 1 to 20 carbon atoms, a haloalkyl group having 1 to 20 carbon atoms, an aryl group having 6 to 40 carbon atoms, an arylalkyl group having 7 to 20 carbon atoms, an arylsilyl group having 6 to 20 carbon atoms, an alkylaryl group having 7 to 20 carbon atoms, an aryloxy group having 6 to 20 carbon atoms, a halogen group, or an amino group.

Moreover, there is provided a method characterized in that the inert solvent may be an aliphatic or alicyclic hydrocarbon solvent having 3 to 13 carbon atoms.

Furthermore, there is provided a method characterized in that the aliphatic or alicyclic hydrocarbon solvent may be n-heptane, isobutane, 2-methyl hexane, 3-methyl hexane, 3-ethyl pentane, 2,3-dimethyl pentane, 2,4-dimethyl pentane, 2,2-dimethyl pentane, 3,3-dimethyl pentane, 2,2,3-trimethyl butane, cyclopropane, cyclopropene, cyclobutane, cyclobutene, cyclopentane, cyclopentene, cyclohexane, cyclohexene, cycloheptane, cycloheptene, cyclooctane, cyclooctene, cyclononane, cyclononene, cyclodecane, cyclodecene, or a mixture thereof.

Advantageous Effects

The present invention can provide a novel catalyst system capable of selectively trimerizing and tetramerizing olefins including ethylene by applying a compound which is not conventionally employed as a ligand compound in a catalyst system for oligomerization of olefins, and can provide a method for preparing 1-hexene and 1-octene with excellent activity and selectivity using the same.

MODE FOR CARRYING OUT THE INVENTION

Hereinafter, preferred embodiments of the present invention will be described in detail. In describing the present invention, if a detailed description relating to well-known technology is considered to obscure the subject matter of the present invention, the detailed description may be omitted. Throughout the specification, a part is referred to "include" an element, the part does not exclude other elements but may further include other elements unless otherwise indicated.

The present invention discloses a catalyst system for olefin oligomerization, the catalyst system including: a ligand compound; a chromium compound; a metal alkyl compound; and an aliphatic or alicyclic hydrocarbon solvent.

The catalyst system for olefin oligomerization according to the present invention is used in an olefin oligomerization method including a step for multimerizing olefins in the presence of the catalyst system. According to the present invention, olefins including ethylene may be selectively trimerized and tetramerized.

Hereinafter, a catalyst system for olefin oligomerization according to a specific embodiment of the present invention will be described in more detail.

In the present invention, the ligand compound is a compound represented by Chemical Formula 1 below:

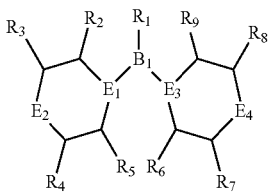

[Chemical Formula 1]

In Chemical Formula 1, $E_1$ and $E_3$ are each independently boron (B), carbon (C), nitrogen (N), silicon (Si) or phosphorus (P), and $E_2$ and $E_4$ are each independently boron (B), carbon (C), nitrogen (N), oxygen (O), silicon (Si), phosphorus (P) or sulfur (S), except that both $E_1$ and $E_2$ are carbon (C) and both $E_3$ and $E_4$ are carbon (C), and preferably $E_1$ may be nitrogen (N) and $E_2$ may be oxygen (O) or $E_3$ may be nitrogen (N) and $E_4$ may be oxygen (O).

In addition, $B_1$ may be aluminum (Al), boron (B), nitrogen (N), or phosphorus (P), and preferably aluminum (Al).

$R_1$ to $R_9$ may be each independently hydrogen, an alkyl group having 1 to 20 carbon atoms, a cycloalkyl group having 3 to 20 carbon atoms, an alkylsilyl group having 1 to 20 carbon atoms, a haloalkyl group having 1 to 20 carbon atoms, an aryl group having 6 to 40 carbon atoms, an arylalkyl group having 7 to 20 carbon atoms, an arylsilyl group having 6 to 20 carbon atoms, an alkylaryl group having 7 to 20 carbon atoms, an aryloxy group having 6 to 20 carbon atoms, a halogen group, or an amino group. Here, the aryl group may be an aromatic hydrocarbon functional group such as phenyl, biphenyl, triphenyl, triphenylene, naphthalenyl, anthracenyl, phenalenyl, phenanthrenyl, fluorenyl, pyrenyl, chrysenyl, perylenyl, and azulenyl, an aromatic heterocyclic functional group such as dibenzothiophenyl, dibenzofuranyl, dibenzoselenophenyl, furanyl, thiophenyl, benzofuranyl, benzothiophenyl, benzoselenophenyl, carbazonyl, indolocarbazolyl, pyridylindolinine, pyrolodipyridinyl, pyrazolyl, imidazolyl, triazolyl, oxazolyl, triazolyl, oxadiazolinyl, oxatriazolyl, dioxazolyl, thiadiazolyl, pyridyl, pyridazinyl, pyrimidyl, pyrazinyl, triazinyl, oxazinyl, oxathiazinyl, oxadiazinyl, indolinine, benzimidazolyl, indazolyl, indoxazinyl, benzoxazolyl, benzisoxazolyl, benzothiazolyl, quinolinyl, isoquinolinyl, cinnolinyl, quinazolyl, quinoxalinyl, naphthyridine, phthalazinyl, pteridinyl, xanthenyl, acridyl, fenazinyl, phenothiazine, phenoxazinyl, benzofuropyridyl, furodipyridyl, benzothienopyridyl, thienopyridyl benzoselenopyridyl, and selenophenodipyridyl, etc.

It is more preferable in terms of stabilization of the central metal that $R_1$ to $R_9$ of Chemical Formula 1 above are each independently hydrogen, an alkyl group having 1 to 20 carbon atoms, a cycloalkyl group, or an aryl group.

As used herein, the term "olefin oligomerization" means that olefin is oligomerized. Depending on the number of olefins to be polymerized, it is called trimerization or tetramerization, and is collectively called multimerization. In particular, the term herein means that 1-hexene and 1-octene are selectively prepared from ethylene.

Also, the term "catalyst system" may refer to any composition, compound, or complex, which exhibits catalytic activity with respect to the "olefin oligomerization" by including the following materials or a reaction product thereof as a catalyst active species, regardless of whether the ligand compound, the chromium compound, the metal alkyl compound, and the aliphatic or alicyclic hydrocarbon solvent are simply mixed, or react with each other to form a separate catalyst active species.

In addition, the selective olefin oligomerization reaction is closely related to the catalyst system used. The catalyst system used during the olefin oligomerization reaction includes a chromium compound serving as a main catalyst and a metal alkyl compound serving as a cocatalyst, wherein the structure of the active catalyst may be changed according to the chemical structure of the ligand, and thus the olefin selectivity and the activity are different.

The present inventors confirmed through experiments that the oligomerization, in particular, the trimerization and the teteramerization of olefin can be performed with high catalytic activity and selectivity, since the electronic and steric environment around the transition metal can be easily controlled by appropriately controlling the ligand compound with the catalyst system for olefin oligomerization, the catalyst system including the ligand compound having the specific structure, the chromium compound, the metal alkyl compound as the cocatalyst, and the aliphatic or alicyclic hydrocarbon as the solvent, and completed the present invention.

In particular, the ligand compound is a hexagonal ring compound in which at least one hetero element such as boron (B), nitrogen (N), oxygen (O), silicon (Si), phosphorus (P), and sulfur (S) is included in the inside of the hexagonal ring or in a functional group connected to the hexagonal ring, and due to such structural characteristics, the ligand compound may be applied to the oligomerization catalyst system of olefin to exhibit high oligomerization reaction activity, and in particular, exhibit high selectivity to 1-hexene and 1-octene. This is assumed to be due to an interaction between adjacent chromium active points.

In the present invention, the chromium compound serves as a main catalyst, and using the chromium(III)- or chromium(II)-containing compound is preferred to be able to increase the reaction activity.

The chromium(III) compound may be, for example, chromium carboxylate, chromium naphthenate, chromium halide, chromium dionate, and more specific examples may include chromium(III) 2,2,6,6-tetramethylheptanedionate, chromium(III) 2-ethylhexanoate, chromium(III) tris (2-ethylhexanoate), chromium(III) naphthenate [Cr(NP)3], bis(2-ethylhexanoate) chromium(III) hydroxide, bis(2-butanoate) chromium(III) hydroxide, chromium(III) chloride, chromic bromide, chromic fluoride, chromium(III) acetylacetonate, chromium(III) acetate, chromium(III) butyrate, chromium (III) neopentanoate, chromium(III) laurate, chromium(III) stearate, chromium(III) oxalate, bis(2-ethylhexanoate) chromium(III) hydroxide, etc.

In addition, specific examples of a chromium(II) compound may include chromous bromide, chromous fluoride, chromous chloride, chromium(II) bis(2-ethylhexanoate), chromium(II) acetate, chromium(II) butyrate, chromium(II) neopentanoate, chromium(II) laurate, chromium(II) stearate, chromium(II) oxalate, etc.

Meanwhile, the chromium compounds may be in a dissolved state in an aliphatic or alicyclic hydrocarbon solvent. The aliphatic or alicyclic hydrocarbon solvent may be, but is not limited to, n-heptane, 2-methyl hexane, 3-methyl hexane, 3-ethyl pentane, 2,3-dimethyl pentane, 2,4-dimethyl pentane, 2,2-dimethyl pentane, 3,3-dimethyl pentane, 2,2,3-trimethyl butane, cyclohexene, cycicoheptane, cycloheptene, cyclooctane, cyclooctene, cyclodecane, cyclodecene, or a mixture thereof.

In the catalyst system for olefin oligomerization of an embodiment, chromium(III) 2-ethylhexanoate, chromium (III) acetylacetonate or bis(2-ethylhexanoate) chromium(III) hydroxide is used as a chromium compound and it is preferable to dissolve and use this in anhydrous cyclohexene solvent in terms of improving the catalytic activity due to the difference in solubility of the solvent.

In the present invention, the metal alkyl compound is a cocatalyst of the catalyst system for olefin oligomerization, and is not particularly limited as long as it can be generally used when multimerizing olefins in the presence of the transition metal catalyst. For example, an alkylaluminum compound, an alkylboron compound, an alkylmagnesium compound, an alkylzinc compound, an alkyllithium compound, etc. may be used as the metal alkyl compound.

However, in order to exhibit high selectivity and activity in the olefin oligomerization reaction, an alkylaluminum compound may be used as the cocatalyst compound. Specific examples of the alkylaluminum compound may include triethylaluminum, tripropylaluminum, tributylaluminum and diethylaluminum chloride, diethylaluminum bromide, diethylaluminum ethoxide, diethylaluminum phenoxide, ethylaluminum dichloride, ethylaluminum sesquichloride, etc., preferably a mixture of triethylaluminum, ethylaluminum dichloride, and ethylaluminum sesquichloride can be used, and this case is preferred because not only can the water be effectively removed, but also the catalytic activity is improved by including the electron donor atom.

In the catalyst system for olefin oligomerization according to the present invention, the molar ratio of the ligand compound:chromium compound:metal alkyl compound may be 0.5:1:1 to 10:1:10,000, and preferably 0.5:1:100 to 5:1:3,000 in order to increase the selectivity to the linear alpha-olefin and increase the multimerization reaction activity. However, the present invention is not limited thereto.

In the present invention, the aliphatic or alicyclic hydrocarbon solvent may be preferably a hydrocarbon solvent having 5 to 20 carbon atoms, and more preferably a hydrocarbon solvent having 5 to 13 carbon atoms.

In addition, in the present invention, the alicyclic hydrocarbon solvent may be a cycloalkene having 5 to 13 carbon atoms including at least one carbon-carbon double bond in a ring, and preferably a cycloalkene having 5 to 13 carbon atoms which satisfies $C_nH_{2n-2}$.

Specific examples of such aliphatic or alicyclic hydrocarbon solvents include n-heptane, 2-methylhexane, 3-methylhexane, 3-ethylpentane, 2,3-dimethylpentane, 2,4-dimethylpentane, 2,2-dimethylpentane, 3,3-dimethylpentane, 2,2,3-trimethylbutane, cyclopropene, cyclobutene, cyclopentene, cyclopentane, cyclohexene, cycloheptene, cycloheptene, cyclooctane, cyclooctene, cyclononene, cyclodecane, cyclodecene or a mixture thereof, etc., preferably cyclopropene, cyclobutene, cyclopentene, cyclohexene, cycloheptene, cyclooctene, cyclononene, cyclodecene or a mixture thereof, and most preferably cyclohexene.

The aliphatic or alicyclic hydrocarbon solvent may be used as a base solvent when mixing the compounds in the preparation of the oligomerization catalyst system, may be used as a diluting solvent when mixing the transition metal compound and the ligand compound, may be a solvent for diluting the cocatalyst, and at the same time may be a solvent used when mixing the transition metal compound, the ligand compound and the cocatalyst. In addition, the aliphatic or alicyclic hydrocarbon solvent may include other organic solvents in addition to these solvents, but preferably may include only the aliphatic or alicyclic hydrocarbon compounds.

In the catalyst system for olefin oligomerization including the ligand compound, the chromium compound, the metal alkyl compound, and the aliphatic or alicyclic hydrocarbon solvent, the three components of the ligand compound, the chromium compound, and the metal alkyl compound may be added together, simultaneously or sequentially in any order thereof, in the aliphatic or alicyclic hydrocarbon solvent, in the presence or absence of monomers to obtain an active catalyst.

Another aspect of the present invention provides a method for preparing an olefin oligomer.

A method for preparing an olefin oligomer according to the present invention includes oligomerizing olefins in an inert solvent that does not react with a catalyst system in the presence of the catalyst system for olefin oligomerization including: a ligand compound represented by Chemical Formula 1 above; a chromium compound; a metal alkyl compound; and an aliphatic or alicyclic hydrocarbon solvent.

The method for preparing an olefin oligomer according to the present invention improves the activity of the reaction by using the catalyst system for olefin oligomerization. In this case, the olefin is preferably an ethylene.

In the present invention, the olefin oligomerization may be performed as a homogeneous liquid phase reaction, a slurry reaction in which the catalyst system is partially or completely insoluble, a two-phase liquid/liquid reaction, a bulk phase reaction in which product olefins serve as main media, or a gas phase reaction in the presence or absence of an inert solvent by using the catalyst system for olefin oligomerization and a conventional apparatus and contacting techniques, and preferably a homogeneous liquid phase reaction may be employed.

The olefin oligomerization reaction may be performed in any inert solvent that does not react with a catalyst compound and an active agent. The inert solvent in the present invention may be an aliphatic or alicyclic hydrocarbon solvent having 3 to 13 carbon atoms. Non-limiting examples of the aliphatic or cycloaliphatic hydrocarbon solvents may include n-heptane, 2-methylhexane, 3-methylhexane, 3-ethylpentane, 2,3-dimethylpentane, 2,4-dimethylpentane, 2,2-dimethylpentane, 3,3-dimethylpentane, 2,2,3-trimethylbutane, cyclopropane, cyclopropene, cyclobutane, cyclobutene, cyclopentane, cyclopentene, cyclohexane, cyclohexene, cycloheptane, cycloheptene, cyclooctane, cyclooctene, cyclononane, cyclononene, cyclodecane, cyclodecene or mixtures thereof, preferably a cycloalkene having 3 to 13 carbon atoms containing at least one carbon-carbon double bond in a ring, more preferably a cycloalkene having 3 to 13 carbon atoms satisfying $C_nH_{2n-2}$, even more preferably a cycloalkene having 5 to 13 carbon atoms satisfying $C_nH_{2n-2}$, and most preferably cyclohexene, cyclooctene or cyclodecene. In this case, the solvent may be used by removing a small amount of water or air that acts as a catalytic poison by treating with a small amount of alkylaluminum.

The olefin oligomerization reaction may be carried out at a temperature of 0 to 250° C., preferably 20 to 200° C., and more preferably 40 to 130° C. It is preferred to allow the reaction to proceed in the above temperature range because too low a reaction temperature may cause an excessively large amount of unwanted insoluble products such as polymers to be produced, and too high a temperature may cause decomposition of the catalyst system and reaction products. In addition, the olefin oligomerization reaction may be carried out at a pressure of 1 to 200 bar, and preferably at a pressure of 10 to 150 bar. Too low a reaction pressure may result in low catalytic activity. In addition, in the process for preparing the olefin oligomer, hydrogen may be added to the reactor at 0.01 to 50 bar, and preferably 0.5 to 10 bar in order to promote the reaction or increase the activity of the catalyst system.

Hereinafter, the present invention will be described in more detail with reference to Examples.

Preparation Example 1: Ligand Compound Preparation

In an inert atmosphere (nitrogen), 2,6-dimethylmorpholine (30 mmol) was dissolved in toluene (60 mL) in a two-neck flask, and the temperature was lowered to 0° C. with ice while stirring. When the temperature was sufficiently lowered, n-butyllithium (66 mmol, 2.5 M in Hexane Aldrich reagent) was slowly added dropwise for 10 minutes. After completing the dropwise addition, the mixture was maintained at 0° C. for 1 hour, and then the ice of the reaction solution was removed to raise the temperature to room temperature. The reactant was stirred and reacted for 12 hours, and after completion of the reaction, the solvent was removed under reduced pressure. Then, the prepared white solid was washed twice with hexane (20 mL) from which water was removed. The washed white solid was dried under reduced pressure and dissolved again in toluene (60 mL). The temperature of the reaction solution was reduced to −78° C. using dry ice, and ethyl aluminum dichloride (15 mmol, 25 wt % in toluene Aldrich reagent) was then slowly added dropwise for 10 minutes. After stirring for 1 hour at the same temperature, the temperature was raised to room temperature, and then the reaction was carried out for 12 hours. After completion of the reaction, the resulting white solid was filtered and then the toluene solvent was removed under reduced pressure. The obtained yellow oil was again dissolved in toluene (4 mL) and recrystallized at −3° C. to prepare a ligand compound represented by Chemical Formula 2 below:

[Chemical Formula 2]

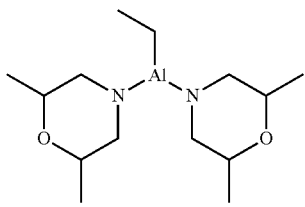

EXAMPLES: CATALYST SYSTEM PREPARATION

Example 1

By using chromium(III) 2-ethylhexanoate (21.3 mmol), ligand compound (63.8 mmol) prepared according to Preparation Example 1 above, ethyl aluminum dichloride (85.1 mmol) and triethylaluminum (319 mmol), a representative catalyst system was prepared in an inert atmosphere (nitrogen). Specifically, chromium(III) 2-ethylhexanoate was dissolved in 30 mL of anhydrous cyclohexene and ligands were added. In a separate container, ethylaluminum dichloride and triethylaluminum were mixed together. The aluminum alkyl solution was then slowly poured into the chromium/ligand solution. The reaction solution was stirred for 5 minutes and then the solvent was removed in vacuum. The remaining oily liquid was diluted to 150 mL with cyclohexene and the solution was filtered to remove black precipitate from the filtrate containing the catalyst system and diluted to a volume of 250 mL with cyclohexene to prepare the final catalyst system.

Example 2

A catalyst system was prepared in the same manner as in Example 1, except that chromium(III) acetylacetonate was used instead of chromium(III) 2-ethylhexanoate in Example 1.

Example 3

A catalyst system was prepared in the same manner as in Example 1, except that bis(2-ethylhexanoate) chromium(III) hydroxide was used instead of chromium(III) 2-ethylhexanoate in Example 1.

Comparative Example

By using chromium(III) 2-ethylhexanoate (21.3 mmol), 2,5-dimethylpyrrole (63.8 mmol), ethyl aluminum dichloride (85.1 mmol) and triethylaluminum (319 mmol), a representative catalyst system was prepared in an inert atmosphere (nitrogen). Specifically, chromium(III) 2-ethylhexanoate was dissolved in 30 mL of anhydrous toluene and ligands were added. In a separate container, ethylaluminum dichloride and triethylaluminum were mixed together. The aluminum alkyl solution was then slowly poured into the chromium/ligand solution. The reaction solution was stirred for 5 minutes, and then the solvent was removed in vacuum. The remaining oily liquid was diluted to 150 mL with cyclohexene and the solution was filtered to remove black precipitate from the filtrate containing the catalyst system and diluted to a volume of 250 mL with toluene to prepare the final catalyst system.

Experimental Example

After filling the 2 L stainless steel reactor with nitrogen, 1 L of anhydrous polymerization solvent shown in Table 1 was added thereto, and 3 mL of triethylaluminum was added thereto, followed by filling with 10 bar of ethylene and raising the temperature to 90° C. After each prepared catalyst solution (30 µmol) was injected to a reactor, ethylene was charged to 35 bar, and the reactant was stirred at a stirring speed of 500 rpm. After one hour, the ethylene feed to the reactor was stopped, the stirring was stopped to stop the reaction and the reactor was cooled down below 10° C. After releasing excess ethylene in the reactor, ethanol mixed with 10 vol % hydrochloric acid was injected into the liquid contained in the reactor. A small amount of organic layer sample was passed through silica gel and dried, and then analyzed by GC-FID. The remaining organic layer was filtered to separate the solid wax/polymer product. These solid products were dried in an 80° C. oven for 8 hours and weighed to obtain polyethylene, and the results are shown in Table 1 below.

TABLE 1

| Division | Anhydrous polymerization solution | Activity (Kg/mmol of cat.) | 1-octene (wt %) | 1-hexene (wt %) | PE (wt %) |
|---|---|---|---|---|---|
| Example 1 | Cyclohexene | 4.2 | 45.3 | 51.2 | 3.5 |

TABLE 1-continued

| Division | Anhydrous polymerization solution | Activity (Kg/mmol of cat.) | 1-octene (wt %) | 1-hexene (wt %) | PE (wt %) |
|---|---|---|---|---|---|
| | Cyclooctene | 3.3 | 47.2 | 49.7 | 3.1 |
| | Cyclocdecene | 3.5 | 43.6 | 53.5 | 2.9 |
| Example 2 | Cyclohexene | 4.3 | 47.1 | 49.7 | 3.2 |
| | Cyclooctene | 3.7 | 48.2 | 48.9 | 2.9 |
| | Cyclocdecene | 3.4 | 46.3 | 50.7 | 3.0 |
| Example 3 | Cyclohexene | 6.1 | 48.8 | 47.7 | 3.5 |
| | Cyclooctene | 4.6 | 50.6 | 46.3 | 3.1 |
| | Cyclocdecene | 5.0 | 49.3 | 47.5 | 3.2 |
| Comparative Example | Cyclohexane | 3.1 | 0 | 99.3 | 0.7 |

As shown in Table 1, as a result of the ethylene oligomerization reaction using the catalyst system according to the present invention, it can be confirmed that 1-hexene and 1-octene can be prepared simultaneously with high selectivity of 90 wt % or more, preferably 95 wt % or more (Examples 1 to 3), and it can be seen to exhibit excellent activity compared to the conventional (Comparative Example).

Hitherto, the preferred examples of the present invention have been described in detail. The description of the present invention is only for illustration, and it could be understood that particular embodiment could be easily changed without changing the technical spirit or essential features of the present invention by one of ordinary skilled in the art.

Accordingly, it should be interpreted that the scope of the present invention is represented by claims hereinafter rather than the detailed description, and all changes or modifications derived from the meaning, range and equivalent concept of claims are included in the scope of the present invention.

The invention claimed is:

1. A catalyst system for olefin oligomerization comprising:
   a ligand compound represented by Chemical Formula 1 below;
   a chromium compound;
   a metal alkyl compound; and
   an aliphatic or alicyclic hydrocarbon solvent,

[Chemical Formula 1]

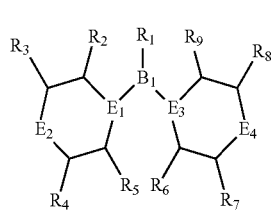

wherein, in Chemical Formula 1, $E_1$ is nitrogen (N) and $E_2$ is oxygen (O), or $E_3$ is nitrogen (N) and $E_4$ is oxygen (O), $B_1$ is aluminum (Al), boron (B), nitrogen (N), or phosphorus (P), $R_1$ to $R_9$ are each independently hydrogen, an alkyl group having 1 to 20 carbon atoms, a cycloalkyl group having 3 to 20 carbon atoms, an alkylsilyl group having 1 to 20 carbon atoms, a haloalkyl group having 1 to 20 carbon atoms, an aryl group having 6 to 40 carbon atoms, an arylalkyl group having 7 to 20 carbon atoms, an arylsilyl group having 6 to 20 carbon atoms, an alkylaryl group having 7 to 20 carbon atoms, an aryloxy group having 6 to 20 carbon atoms, a halogen group, or an amino group.

2. The catalyst system of claim 1,
   wherein the chromium compound is a compound containing chromium(III) or chromium(II).

3. The catalyst system of claim 1,
   wherein the metal alkyl compound is at least one selected from the group consisting of an alkylaluminum compound, an alkylboron compound, an alkylmagnesium compound, an alkylzinc compound, and an alkyllithium compound.

4. The catalyst system of claim 1,
   wherein the molar ratio of the ligand compound, the chromium compound, and the metal alkyl compound is 0.5:1:1 to 10:1:10,000 with respect to the chromium compound.

5. A method for preparing an olefin oligomer, the method comprising oligomerizing olefins in an inert solvent that does not react with a catalyst system in the presence of the catalyst system for olefin oligomerization according to claim 1.

6. The method of claim 5,
   wherein the olefin oligomerization comprises a trimerization and a tetramerization.

7. The method of claim 5,
   wherein the inert solvent is an aliphatic or alicyclic hydrocarbon solvent having 3 to 13 carbon atoms.

8. The method of claim 7,
   wherein the aliphatic or alicyclic hydrocarbon solvent is n-heptane, isobutane, 2-methyl hexane, 3-methyl hexane, 3-ethyl pentane, 2,3-dimethyl pentane, 2,4-dimethyl pentane, 2,2-dimethyl pentane, 3,3-dimethyl pentane, 2,2,3-trimethyl butane, cyclopropane, cyclopropene, cyclobutane, cyclobutene, cyclopentane, cyclopentene, cyclohexane, cyclohexene, cycloheptane, cycloheptene, cyclooctane, cyclooctene, cyclononane, cyclononene, cyclodecane, cyclodecene, or a mixture thereof.

9. A catalyst system for olefin oligomerization comprising:
   a ligand compound represented by Chemical Formula 1 below;
   a chromium compound;
   a metal alkyl compound; and
   an aliphatic or alicyclic hydrocarbon solvent,

[Chemical Formula 1]

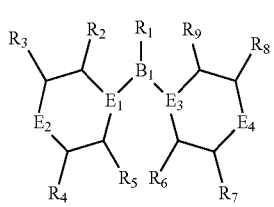

wherein, in Chemical Formula 1, $E_1$ and $E_3$ are boron (B), carbon (C), nitrogen (N), silicon (Si), or phosphorus (P), and $E_2$ and $E_4$ are boron (B), carbon (C), nitrogen (N), oxygen (O), silicon (Si), phosphorus (P), or sulfur (S), except that both $E_1$ and $E_2$ are carbon (C) and both $E_3$ and $E_4$ are carbon (C), $B_1$ is aluminum (Al), boron (B), nitrogen (N), or phosphorus (P), $R_1$ to $R_9$ are each independently hydrogen, an alkyl group having 1 to 20 carbon atoms, a cycloalkyl group having 3 to 20 carbon atoms, an alkylsilyl group having 1 to 20 carbon atoms, a haloalkyl group having 1 to 20 carbon atoms, an aryl group having 6 to 40 carbon atoms, an arylalkyl group having 7 to 20 carbon atoms, an arylsilyl group having 6 to 20 carbon atoms, an alkylaryl group having 7 to 20 carbon atoms, an aryloxy group having 6 to 20 carbon atoms, a halogen group, or an amino group, and wherein the alicyclic hydrocarbon solvent is a cycloalkene having 5 to 13 carbon atoms.

10. The catalyst system of claim 9, wherein the aliphatic or alicyclic hydrocarbon solvent is n-heptane, 2-methyl hexane, 3-methyl hexane, 3-ethyl pentane, 2,3-dimethyl pentane, 2,4-dimethyl pentane, 2,2-dimethyl pentane, 3,3-dimethyl pentane, 2,2,3-trimethyl butane, cyclopropene, cyclobutene, cyclopentene, cyclopentane, cyclohexene, cycloheptane, cycloheptene, cyclooctane, cyclooctene, cyclononene, cyclodecane, cyclodecene, or a mixture thereof.

11. A method for preparing an olefin oligomer, the method comprising oligomerizing olefins in an inert solvent that does not react with a catalyst system in the presence of the catalyst system for olefin oligomerization according to claim 9.

12. The method of claim 11, wherein the olefin oligomerization comprises a trimerization and a tetramerization.

* * * * *